US00PP19061P3

(12) United States Plant Patent
Olesen

(10) Patent No.: US PP19,061 P3
(45) Date of Patent: Aug. 5, 2008

(54) MINIATURE ROSE PLANT NAMED 'POULPAH038'

(50) Latin Name: *Rosa* hybrid
Varietal Denomination: Poulpah038

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 259 days.

(21) Appl. No.: 11/389,468

(22) Filed: Mar. 23, 2006

(65) Prior Publication Data

US 2007/0226849 P1 Sep. 27, 2007

(51) Int. Cl.
*A01H 5/00* (2006.01)

(52) U.S. Cl. ..... Plt./116

(58) Field of Classification Search ..... Plt./116, Plt./122

See application file for complete search history.

*Primary Examiner*—Annette H Para

(57) ABSTRACT

A new miniature rose plant that has abundant, red striped flowers and attractive foliage. The variety successfully propagates from softwood cuttings and is suitable for year-round production in commercial glasshouses. This new and distinct variety has shown to be uniform and stable in the resulting generations from asexual propagation.

2 Drawing Sheets

Botanical designation: *Rosa* hybrid.
Variety denomination: 'Poulpah038'.

SUMMARY OF THE INVENTION

The present invention constitutes a new and distinct variety of miniature rose plant which originated from a controlled crossing between the female seed parent, 'Poulgrad' U.S. Plant Pat. No. 11,610, and the male pollen parent an unnamed seedling.

The two parents were crossed during the summer of 1998 and the resulting seeds were planted in a controlled environment in Fredensborg, Denmark. The new variety, named 'Poulpah038', originated as a single seedling from the stated cross.

The new variety may be distinguished from its female seed parent by the following combination of characteristics:

1. The seed parent has a petal count of 25 to 30 petals. 'Poupah038' has 17 to 18 petals, 1 to 2 of which are petaloids.
2. Flowers of the seed parent have a general tonality of Red Group 53A to Red Group 46A. Flowers of 'Poulpah038' are Red Group 42A to 43A with streaks of Red Group 38B to 38C.

The new variety may be distinguished from its male pollen parent by the following combination of characteristics:

1. The pollen parent has flowers which are 35 to 40 mm in diameter. Flowers of 'Poulpah038' are normally 45 mm in diameter.
2. Flowers of the pollen parent are generally colored Red with white and yellow color streaks. Flowers of 'Poulpah038' are Red Group 42A to 43A with streaks of Red Group 38B to 38C.

The objective of the hybridization of this rose variety for commercial culture was to create a new and distinct variety with unique qualities, such as:

1. Uniform and abundant red striped flowers;
2. Vigorous and compact growth;

3. Durable flowers and foliage which make a variety suitable for distribution in the floral industry;
4. Excellent disease resistance.

This combination of qualities is not present is previously available commercial cultivars of this type, known to the inventor, and distinguish 'Poulpah038' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah038' was selected by the inventor as a single plant from the progeny of the hybridization in 1998.

Asexual reproduction of 'Poulpah038' by cuttings and traditional budding was first done by Mogens N. Olesen in the nursery in Fredensborg, Denmark in 1999. This initial and other subsequent propagations conducted in controlled environments have demonstrated that the characteristics of 'Poulpah038' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpah038'. Specifically illustrated in the drawing.

DETAILED DESCRIPTION OF THE VARIETY

Figures 1A, 1B, 1C, 1D, 1E:
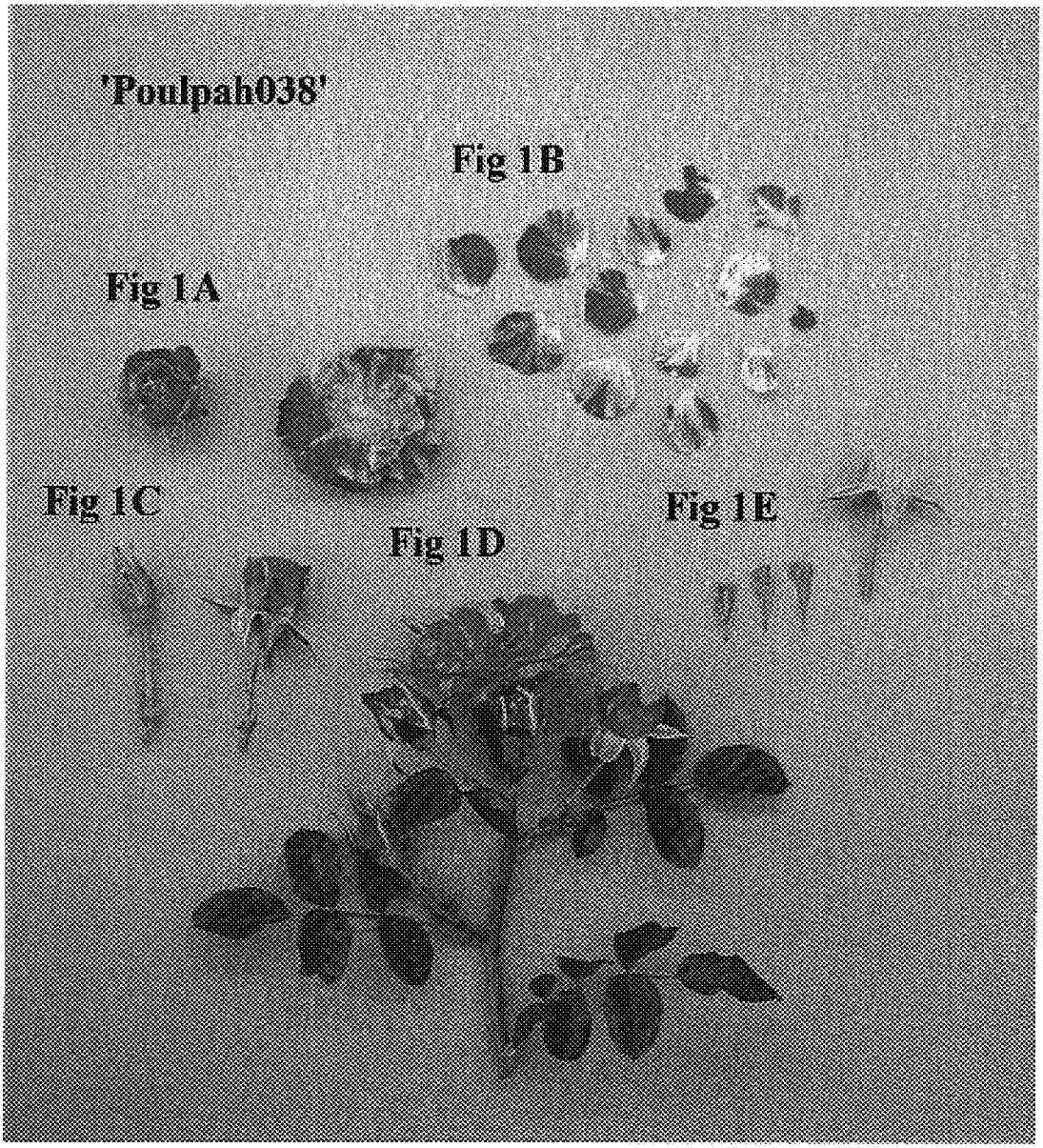
FIG. 1A; Open flowers.
FIG. 1B; Flower petals, detached.
FIG. 1C; Flower bud and partially open flower.
FIG. 1D; Cluster of open flowers attached to stem.
FIG. 1E; Sepals, receptacle, pedicel and reproductive flower parts.
Figures 2A, 2B, 2C, 2D:
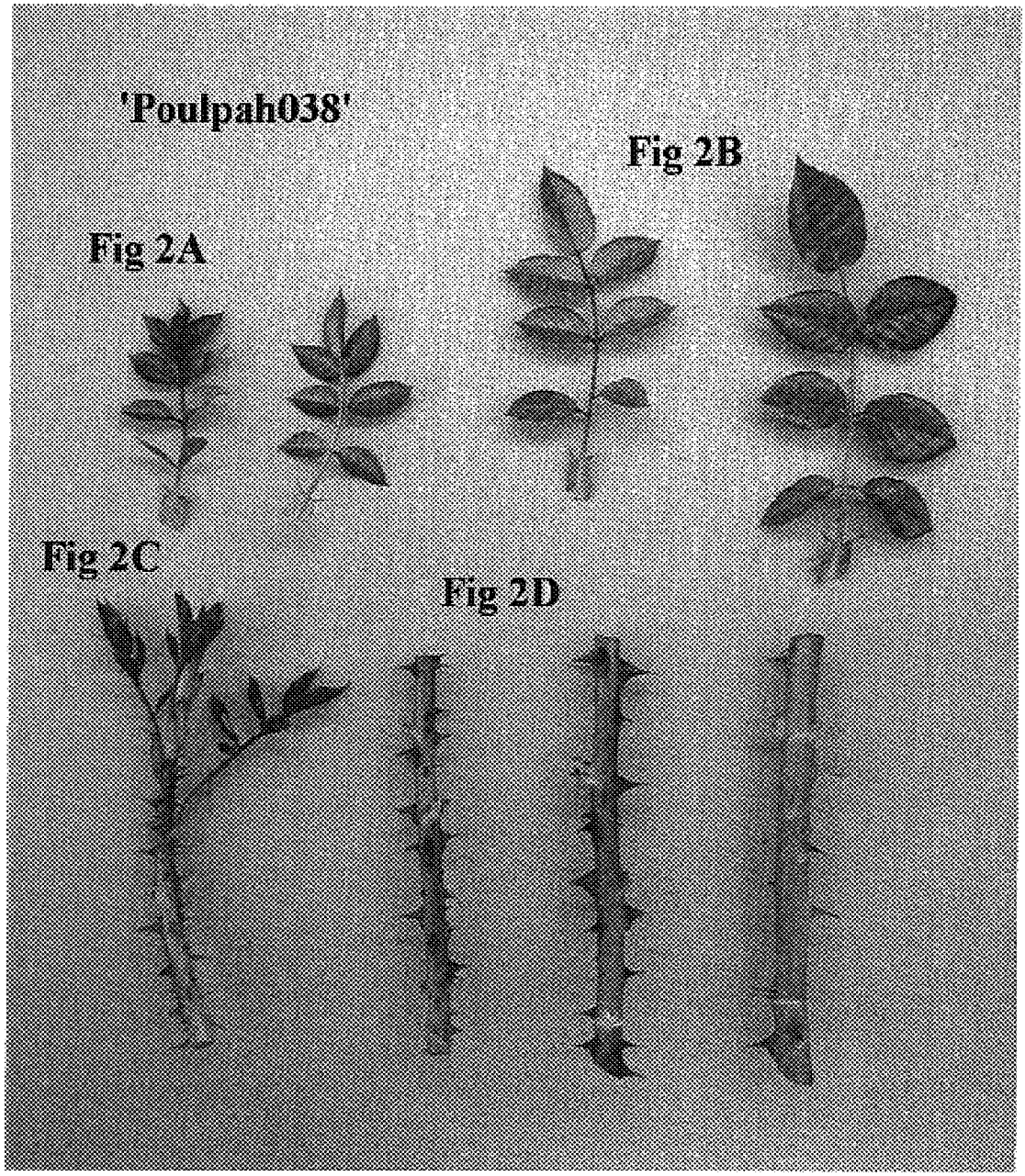
FIG. 2A; Juvenile leaves, showing anthocyanin.
FIG. 2B; Mature leaves.
FIG. 2C; Juvenile leaves and stem.
FIG. 2D; Intermediate and mature bare stems.

The following is a description of 'Poulpah038', as observed in its growth in Jackson County, Oreg. Observed plants are 2 years of age and were cultivated in an open field grown on *Rosa multiflora* understock. Color references are made using the Royal Horticultural Society (London, England) Colour Chart, 2003, except where common terms of color are used.

For a comparison, several physical characteristics of the rose variety 'Poulcub', described in U.S. Plant patent application Ser. No. 10/647,010 dated Aug. 21, 2003, now abandoned, are compared to 'Poulpah038' in Chart 1.

CHART 1

| | 'Poulpah038' | 'Poulcub' |
|---|---|---|
| Petalage: | 17 to 18 petals, 1 to 2 of which are petaloids | 15 to 18 petals with 20 petaloids |
| Leaflet dimensions: | 37 mm long × 19 mm wide | 20 mm in length by 10 mm wide |
| Color of filaments: | Yellow Group 13A | Yellow-Orange Group 17B |

FLOWER AND FLOWER BUD

Blooming habit: Continuous.

Flower bud:

*Size.*—Upon opening, 18 mm in length from base of receptacle to end of bud. Normally 12 mm in diameter.

*Bud form.*—Pointed ovate to broad based.

*Bud color.*—As sepals unfold, petals are distinctly Orange-Red Group 33A, Orange Group 27A, Red Group 41A, and Yellow Group 11C.

*Sepals.*—Upper Surface: Color: Green Group 138B. Strong anthocyianic pigments Greyed-Red Group 178A. Texture: Strongly Pubescent. Lower Surface: Color: Yellow-Green Group 146C. Anyocyanic pigments Greyed-Red Group 178A. Texture: Smooth with few stipitate glands. Shape: Apex: Cirrhose. Base: Flat at union with receptacle. Margins: Margins have medium to weak foliaceous appendages on three of the five sepals. Stipitate glands are present in medium quantity. Size: 19 to 20 mm long by 6 to 7 mm wide.

*Receptacle.*—Surface Texture: Smooth. Shape: Urn-shaped. Size: 6 mm (h)×7 to 8 mm (w). Color: Yellow-Green Group 144A. Anthocyanin: Greyed-Red Group 178A to 178B.

*Peduncle.*—Surface: Smooth. Color: Yellow-Green Group 146B. Anthocyanin: Greyed-Orange Group 177A. Diameter: Normally 3 mm. Length: 35 to 110 mm.

*Pedicel.*—Surface: Very rough with stipitate glands and small prickles. Length: 30 to 35 mm average length. Diameter: 2.5 mm on average. Color: Yellow-Green Group 144B. Anythocyanin: Light anthocyanic pigments of Greyed-Red Group 178B. Strength: Medium strength.

*Borne.*—In clusters of 3 to 10 buds per flowering stem. Inflorescence type is a corymb.

Flower bloom:

*Fragrance.*—Light floral scent.

*Duration.*—The blooms have a duration on the plant of approximately 7 to 10 days. Petals fall cleanly away from plant after flowers have fully matured.

*Size.*—Normally 45 mm when open. Average flower diameter is 13 mm.

*Form.*—General shape is a semi-double and fully open and almost flat.

Petalage: There are normally 17 to 18 petals, 1 to 2 of which are petaloids.

Color:

*Upon opening, petals.*—Outermost petals: Upper Surface: Red Group 42A to 43A with streaks of Red Group 38B to 38C. Basal zone streaks are Yellow Group 9B. Lower Surface: Red Group 47C with streaks of Orange-Yellow Group 19D to Orange Group 27C.

*Upon opening, basal petal spots.*—Upper Surface: Yellow Group 9B. Lower Surface: Yellow Group 9D.

*After opening petals.*—Outermost petals: Upper Surface: Red Group 42A to 43A with streaks of Red Group 38B to 38C. Basal zone streaks are Yellow Group 9B. Lower Surface: Red Group 47C with streaks of Orange-Yellow Group 19D to Orange Group 27C.

General tonality: Red Group 42A to 43A with streaks of Red Group 38B to 38C.

Petals:

*Petal reflex.*—Slightly reflexed.

*Petal margin.*—Normally entire. Occasionally petal margins have a large cleft. Medium undulations of margin observed.

*Shape.*—Broad elliptical. Base: Rounded. Apex: Acute.

*Size.*—Normally 17 to 20 (l)×16 to 23 mm (w).

*Texture.*—Smooth.

*Thickness.*—Average.

*Arrangement.*—Not formal.

Petaloids:

*Quantity.*—Normally, there are 1 to 2.

*Size.*—11 mm long; 7 mm wide.

*Shape.*—Narrow elliptical. Base: Acute. Apex: Rounded.

*Color.*—Red Group 42A to 43A with streaks of Red Group 38B to 38C.

Reproductive organs:

*Pollen.*—None observed.

*Anthers.*—Size: 2 mm long. Color: Yellow-Orange Group 16B. Quantity: 60 to 70.

*Filaments.*—Color: Yellow Group 13A. Length: 6 mm.

*Pistils.*—Length: 3 mm long. Quantity: 45 to 50.

*Stigmas.*—Slightly inferior relative to the length of the filaments and the height of the anthers. Color: Yellow-Green Group 154D.

*Styles.*—Color: Yellow-Green Group 154D with intonations of Red Group 39B.

*Seed formation.*—Not observed.

PLANT

Plant growth: Compact, upright to bushy. When grown on *Rosa multiflora* understock, the average height of the plant itself is 65 to 75 cm and the average width is 60 cm.

Stems:

*Color.*—Young wood: Yellow-Green Group 146C. Anthocyanic intonations of Greyed-Orange Group 176B. Older wood: Yellow-Green Group 146B.

*Internodal distance.*—On mature canes, average distance between nodes is 40 to 45 mm.

*Length of stems.*—On average, canes are 45 to 50 cm from the base of the stem to the flowering portion.

*Diameter.*—7 to 10 mm.

*Surface texture.*—Young wood: Rough with many prickles. Older wood: Smooth.

Prickles:

*Incidence.*—8 to 10 per 10 cm of stem on mature wood.

*Size.*—Average length: 10 to 11 mm.

*Color.*—Juvenile prickles are Greyed-Purple Group 183A. Mature prickles are Greyed-Orange Group 164B.

Plant foliage: Normal number of leaflets on normal leaves in middle of the stem: 7 leaflets.

*Compound leaf size.*—130 mm (l)×70 mm (w).

*Quantity.*—2 to 3 leaves per 10 cm of stem.

*Color:*

*Juvenile foliage.*—Upper Leaf Surface: Yellow-Green Group 146B to 146C. Lower Leaf Surface: Yellow-Green Group 146D. Anthocyanic intonations: Greyed-Red Group 178A, generalized.

*Mature foliage.*—Upper Leaf Surface: Yellow-Green Group 147A. Lower Leaf Surface: Yellow-Green Group 147B.

Plant leaves and leaflets:

*Stipules.*—Size: Normally 15 mm. Shape: Linear, slightly broad based with outward extending apecies. Margins: Finely serrated with many stipitate glands. Color: Green Group 137B.

*Petiole.*—Length: Normally 27 mm. Diameter: 2 mm on average. Upper surface: Color: Yellow-Green Group 146B. Observations: Numerous stipitate glands observed. Lower surface: Color: Yellow-Green Group 144A to 144B. Observations: Numerous prickles observed.

*Rachis.*—Size: 66 mm in length. Upper Surface: Color: Yellow-Green Group 146B. Observations: Numerous stipitate glands. Lower Surface Color: Yellow-Green Group 144A to 144B. Observations: Numerous prickles observed.

*Leaflet.*—Size: Normally 37 mm in length by 19 mm wide. Edge: Finely serrated. General Shape: Elliptical. Apex Shape: Obtuse and cordate. Base Shape: Acuminate. Texture: Smooth. Thickness: Average. Arrangement: Odd pinnate. Venation: Reticulate. Leaf Gloss: Somewhat glossy finish.

Disease resistance: Above average resistance to powdery and downy mildew, black spot, and *Botrytis* under normal growing conditions in Jackson County Oreg.

It is claimed:

1. A new and distinct variety of rose plant of the miniature class named 'Poulpah038', substantially as illustrated and described herein, due to its durable and abundant, red striped flowers, vigorous growth, compact habit, and disease resistance that makes the variety suitable for distribution in the nursery and floral industry.

* * * * *

'Poulpah038'

'Poulpah038'